United States Patent [19]
Takach

[11] Patent Number: 5,609,149
[45] Date of Patent: Mar. 11, 1997

[54] ANTI-CHOKE DEVICE

[76] Inventor: Stephen J. Takach, 3 Durban Ave., Hopatcong, N.J. 07843

[21] Appl. No.: 539,332

[22] Filed: Oct. 4, 1995

[51] Int. Cl.⁶ .................................................. A61M 16/00
[52] U.S. Cl. .................. 128/200.24; 128/206.26
[58] Field of Search ................... 128/220.24, 205.19, 128/205.24, 205.18, 206.26; D23/231

[56] References Cited

U.S. PATENT DOCUMENTS

| | | | |
|---|---|---|---|
| 3,461,866 | 8/1969 | Ritchie | 128/205.18 |
| 3,939,830 | 2/1976 | Da Costa | 128/205.18 |
| 4,082,095 | 4/1978 | Mendelson et al. . | |
| 4,287,819 | 9/1981 | Emerit . | |
| 4,971,053 | 11/1990 | Tarrats | 128/205.19 |
| 5,167,621 | 12/1992 | Band et al. . | |
| 5,254,086 | 10/1993 | Palmer et al. . | |
| 5,305,743 | 4/1994 | Brain | 128/200.24 |

FOREIGN PATENT DOCUMENTS

| | | | |
|---|---|---|---|
| 668573 | 11/1929 | France . | |
| 746185 | 5/1933 | France . | |
| 230740 | 2/1911 | Germany . | |
| 97293 | 1/1961 | Norway | 128/205.18 |
| 399657 | 3/1966 | Switzerland | 128/205.18 |

*Primary Examiner*—Edgar S. Burr
*Assistant Examiner*—Daniel J. Colilla

[57] ABSTRACT

A suction device for withdrawing an object obstructing the breathing passage of a choking victim. The device includes a vacuum pump comprising a cylinder housing a flexible plunger, an external for moving the plunger, and a face mask for applying vacuum to the face of the victim. The face mask seals the user's face against vacuum leakage. Optionally, the device has a conduit connecting the vacuum pump to the face mask, thereby enabling remote location of the face mask relative to the vacuum pump. The plunger is resilient and flexible, so that it deflects responsive to excessive vacuum, permitting air to bypass the plunger when deflecting. Vacuum is thus limited, in order to prevent injury such as collapsed lungs. Blockage of the device by the obstructing object after withdrawal by suction is prevented by a strainer. Obstruction of the plunger by an object entering the bottom of the cylinder is prevented by a grate protecting the open bottom. A flange having holes for accepting fasteners enables the suction device to be firmly mounted to an environmental surface. The novel suction device is convenient for persons who are apt to choke on food, or for fixed mounting in a place where many people periodically dine, such as a restaurant.

16 Claims, 3 Drawing Sheets

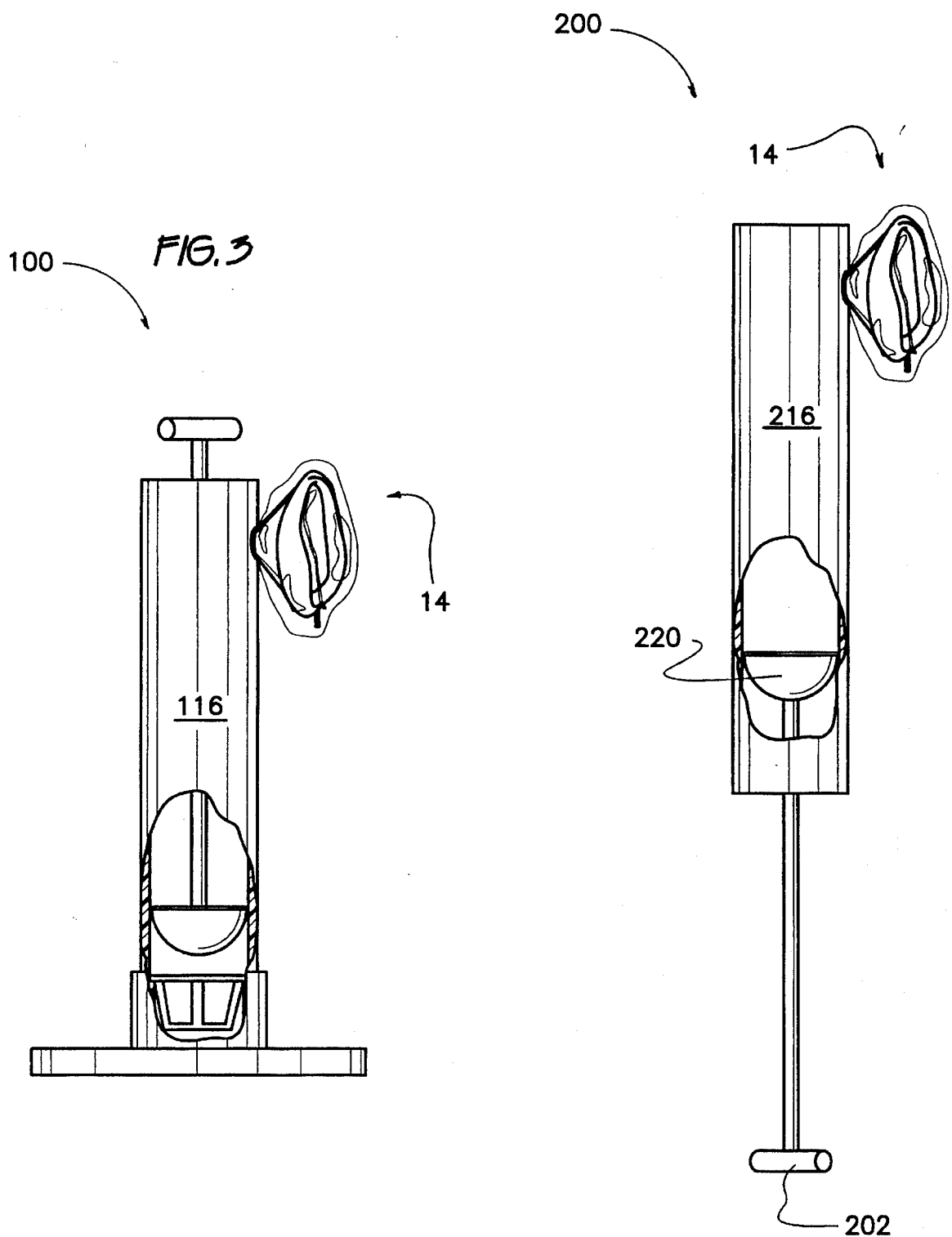

ANTI-CHOKE DEVICE

BACKGROUND OF THE INVENTION

1. Field of the Invention

The present invention relates to a suction inducing device for clearing the throat of a person choking on a food particle. The device includes a manual pump developing partial vacuum on its downstroke, and tubes and attachments for holding the device against the victim's mouth. The pump limits maximum partial vacuum by deflecting responsive to pressure differential between ambient pressure and the partial vacuum.

The pump comprises a flexible plunger disposed within a cylinder. The flexible plunger yields or deflects when moved with sufficient speed, so as to allow some air to flow past it into the chamber developing vacuum. This limited vacuum is a safety feature which prevents injury to the user, such as collapsing a lung.

Tubes are provided for connecting the face mask to the cylinder, where it is desired that the face mask be remotely located. These tubes, or necks, may be of different lengths, and may include both flexible and rigid necks.

The device has a trap for preventing blockage of the vacuum pump by objects removed by vacuum. A screen prevents blockage of the cylinder at an open end by a foreign object. The device includes mounting structure for mounting to vertical and horizontal environmental surfaces.

2. Description of the Prior Art

From time to time, a person will choke on a food particle or other object which may become lodged in his or her throat. If not cleared by spontaneous coughing or other actions, intervention by others may be required to remove the object causing choking. It has become recommended practice in emergency medical circles to employ the Heimlich maneuver, in which a second person suddenly squeezes the victim's torso below from behind the body and beneath the rib cage. This maneuver creates pressure in the lungs which will hopefully expel the object.

However, the Heimlich maneuver is not always successful. It is possible that the victim cannot be moved into a position enabling appropriate positioning of the would-be rescuer, or may be too heavy to move into an appropriate position. A second possible cause of failure of the Heimlich maneuver is that the victim lacks sufficient air in the lungs to develop enough pressure to expel the object. This could arise from having ingested the object immediately upon completing an exhaling step in the breathing cycle, or from having exhaled air by coughing.

In these situations, placing a source of suction to the mouth of the victim may prove more effective than by creating positive pressure, with respect to ambient pressure, within the torso.

Hand operated pneumatic pumps have long been employed for distributing and removing fluent material. An example is seen in U.S. Pat. No. 4,082,095, issued to Barry Mendelson et al. on Apr. 4, 1978. The device of Mendelson et al. does not develop vacuum on the downstroke of the piston, unlike the present invention. This device lacks a flexible plunger for relieving excess vacuum, a face mask for sealing pneumatic pressure at the face of a user, a trap for catching expelled material from the victim, a grate for preventing clogging of the piston chamber while simultaneously enabling air to be expelled to the ambient atmosphere, and means for mounting on an environmental surface. By contrast, these elements are present in the present invention.

U.S. Pat. No. 4,287,819, issued to André A. C. Emerit on Sep. 8, 1981, describes a vacuum device which develops vacuum when the handle is lifted relative to the cylinder. This is opposite the arrangement of the present invention. The Emerit device further lacks a flexible plunger for relieving excess vacuum, a face mask for sealing pneumatic pressure at the face of a user, a trap for catching expelled material from the victim, a grate for preventing clogging of the piston chamber while simultaneously enabling air to be expelled to the ambient atmosphere, and means for mounting on an environmental surface. By contrast, these elements are present in the present invention.

A fluid extractor described in U.S. Pat. No. 5,167,621, issued to David M. Band et al. on Dec. 1, 1992, generates vacuum by subjecting a diaphragm to an external source of vacuum. By contrast, the present invention employs a plunger disposed within a cylinder to generate vacuum. The device of Band et al. lacks means for relieving excess vacuum, a trap for catching expelled material from the victim, a grate for preventing clogging of the piston chamber while simultaneously enabling air to be expelled to the ambient atmosphere, and means for mounting on an environmental surface. By contrast, these elements are present in the present invention. While the device of Band et al. includes a mouthpiece, this is different from the face mask of the present invention, which seals pneumatic pressure at the face of a user subjected to vacuum for extracting a foreign object from the breathing passageways.

In U.S. Pat. No. 5,254,086, issued to Darrel Palmer et al. on Oct. 19, 1993, a dual pressure and vacuum device having two cylinders is set forth. Valves of the two cylinders are interdependent, relying upon pressure differential for successful operation. By contrast, the present invention has but one cylinder. Interdependent valves are not present in the present invention. The invention of Palmer et al. lacks a flexible plunger for relieving excess vacuum, a face mask for sealing pneumatic pressure at the face of a user, a trap for catching expelled material from the victim, a grate for preventing clogging of the piston chamber while simultaneously enabling air to be expelled to the ambient atmosphere, and means for mounting on an environmental surface. By contrast, these elements are present in the present invention.

French Pat. Nos. 668,573, dated November 1929, illustrates a positive pressure device. By contrast, the present invention generates vacuum. The subject device of the French patent lacks means for relieving excess vacuum, the protected opening of the cylinder of the present invention wherein air is rejected to the ambient, a face mask capable of sealing vacuum at the user's mouth and nose, and a plunger disposed within a cylinder. By contrast, these elements are present in the instant invention.

Although the device illustrated in French Pat. No. 746,185, dated May, 1933, has a plunger disposed within a cylinder, it is a positive pressure device which lacks structure for employing vacuum generated on a downstroke, and a plunger designed to limit vacuum. By contrast, both characteristics are found in the present invention. This prior art device also lacks an inflatable face mask for sealing pneumatic pressure at the face of a user, a trap for catching expelled material from the victim, a grate for preventing clogging of the piston chamber while simultaneously enabling air to be expelled to the ambient atmosphere, and means for mounting on an environmental surface. By contrast, these elements are present in the present invention.

German Pat. No. 230,740, dated February, 1911, further illustrates the art of manual pneumatic pumps. This device fails to teach a plunger which deflects to relieve excess vacuum, a protected opening within the cylinder for discharging air to the ambient atmosphere, a trap for catching an object removed by vacuum, and structure for mounting on an environmental surface. By contrast, these features are included in the present invention.

None of the above inventions and patents, taken either singly or in combination, is seen to describe the instant invention as claimed.

SUMMARY OF THE INVENTION

The present invention is directed to a manually operated plunger type suction device for clearing a food particle from the breathing passage of a person. To this end, the novel construction incorporates features which are critical to the purposes of the present invention, but which have little relevance to the purposes of prior art devices. An example is the arrangement of the neck connecting a mouthpiece to the vacuum source. The neck communicates with the upper chamber of the plunger cylinder, rather than with the lower chamber, as is normally practiced in the prior art. Because of this arrangement, sudden, swift depression of the plunger induces a strong partial vacuum which is useful in clearing a lodged obstruction from the throat, but which is insignificant in liquid suction applications.

Excessive vacuum, which could be harmful to the victim, is limited by construction of the plunger inducing vacuum. The plunger deflects or yields if excess vacuum is developed, thereby allowing air to bypass the plunger and relieve the vacuum. This prevents injury to the victim, such as collapse of the lungs.

Another advantage of this arrangement is that in one embodiment of the invention, it is possible for a person to self-administer suction in the absence of others who could otherwise assist. In this embodiment, the neck is rigid. The face is advantageously located close to the hands, so that the victim can place his or her mouth over the mouthpiece, then rapidly thrust the plunger downwardly. This is a convenient, easily performed operation, which does not require grasp of the device to locate the mouthpiece properly. The only necessary grasp is of the handle, for depressing the plunger. The downward motion is more comfortable and natural for the body than would be an upward pull on the plunger handle.

The present invention is usable either mounted to an environmental surface, or not fixed to the environment. It is preferable for self-administration that the device be fixed. In a portable condition, the device may be carried to emergency sites by emergency personnel. A long, flexible neck is preferable in the latter example, so that the device may be immediately deployed, particularly if the victim is not easily positioned for effective contact with the device.

The novel food extractor has a removable base enabling fixed mounting to an environmental surface, and a grate for preventing ingress of foreign objects into the lower chamber. Thus, obstruction of the downward stroke of the piston is prevented. A strainer is provided in series within each of several optional necks, so that the obstructing object, if sucked from the victim's mouth, will not enter the cylinder and thus require disassembly thereof.

Rigid and flexible necks are both included, so that the invention may be practiced in the form of a modular kit. Both types of necks are compatible with commercially available mouthpieces.

The device includes an external carrying handle and a cap for covering the plunger handle.

Accordingly, it is a principal object of the invention to provide a manual suction device for clearing the throat of an object causing choking.

It is another object of the invention to enable rapid, forceful evacuation of the vacuum chamber by a downstroke of a piston.

Another object of the invention is to limit vacuum developed by the piston to a degree safe for a person.

It is a further object of the invention to locate a mouthpiece in a position convenient for self-administration of suction.

Still another object of the invention is to provide a trap for catching the clogging object prior to entry into the vacuum cylinder, should the object be ingested into the suction device.

An additional object of the invention is to prevent obstruction of the piston on its downstroke.

It is again an object of the invention to provide a plurality of necks for selective rigid and flexible attachment of a mouthpiece to the suction device.

Yet another object of the invention is to enable solid or fixed mounting of the suction device to an environmental surface.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 3 is a side elevational view of an alternative embodiment of the invention, partially broken away to reveal internal detail.

FIG. 4 is a side elevational view of another alternative embodiment of the invention, partially broken away to reveal internal detail.

DETAILED DESCRIPTION OF THE PREFERRED EMBODIMENTS

Figure 1:
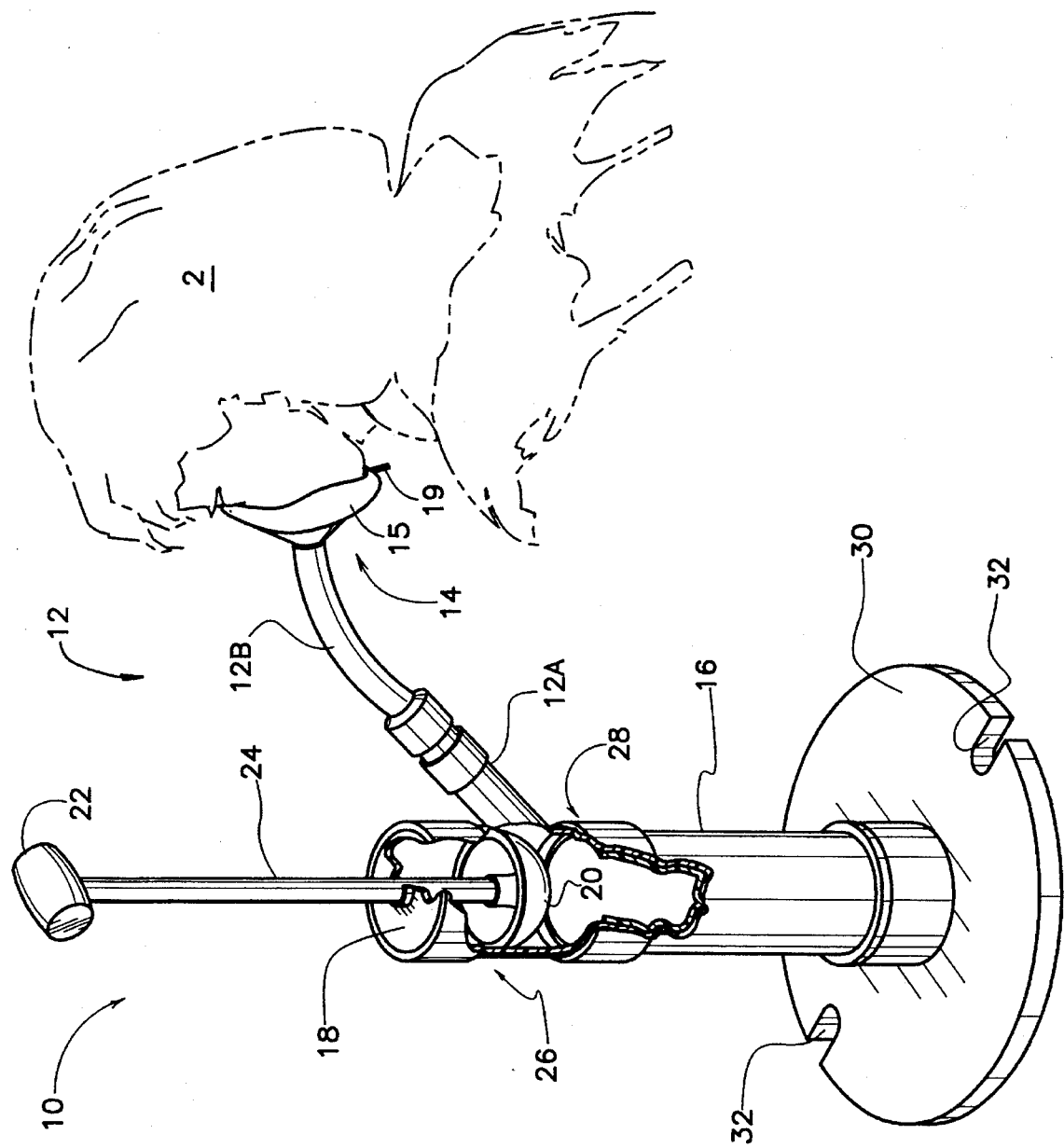
FIG. 1 is an environmental, perspective view of the invention, partially broken away to reveal internal detail.

As seen in FIG. 1, novel suction device 10 is seen as it would be employed by a person 2. Suction device 10 comprises a pump for generating vacuum, from which projects an optional conduit or neck 12 conducting suction or vacuum to a face mask 14. Face mask 14 is of conventional, known construction, having a flexible, circular, inflatable member 15 for placing over and conforming to a person's mouth and nose in order to exclude air flow communication between the person's air passages and the ambient atmosphere.

Face mask 14 is enclosed within a protective membrane 17 for maintaining a sterile condition. Membrane 17 is removed immediately prior to each usage, so that contamination of the user is precluded. A new face mask 14 is installed on device 10 and inflated after each usage, so that device 10 need only have membrane 17 removed to be prepared for a subsequent usage.

An inflation tube 19 projects from face mask 14, for inflating the face contacting member 15. Tube 19 enables oral inflation, and is located so as not to be covered by membrane 17. Therefore, inflation may be performed immediately upon installation of a new face mask 14. Membrane 17 is thus not disturbed during inflation, and may be removed only when a need for device 10 arises.

Face mask 14 includes an opening (not shown) for attachment to a tube, such as a neck portion 12B or 12C, so that face mask 14 is manually attached to respiration equipment. In this manner, face mask is readily manually installed on device 10.

Face mask 14 connects breathing passages of the user or victim to vacuum generated within suction device 10, and prevent excessive leakage at the victim's face which would defeat effectiveness of suction device 10. With the mouth and nose area pressed against face mask 14, ambient air is prevented from relieving the vacuum within face mask 14. Vacuum will therefore remove foreign objects (not shown) which may have become lodged within the victim's throat.

It is appreciated that in the strictest sense, suction and vacuum do not actually exist. These terms are abstract concepts signifying that pressure present within suction device 10 is reduced from ambient pressures, and are employed herein for convenience and brevity.

Suction device 10 comprises a cylinder 16 sealed at its proximal end by a cap 18. The distal end of cylinder 16 is open to the atmosphere. A plunger 20 is slidably disposed within cylinder 16, and is connected to a handle 22 by a shaft or rod 24, which passes through cap 18. Of course, handle 22 is located outside cylinder 16 for accessibility. Plunger 20 divides cylinder 16 into an upper chamber 26 located above the upper side of plunger 20, and a lower chamber 28 located below the lower side of plunger 20.

Vacuum is generated within chamber 26 when plunger 20 is rapidly forced downwardly, as depicted in FIG. 1, by moving handle 22. Air which would otherwise be compressed and resist the stroke of plunger 20 is expelled from chamber 28, through the open distal end of cylinder 16. Conducted through face mask 14, vacuum thus effectively acts on the choking victim.

As plunger 20 moves downwardly, vacuum is generated within chamber 26, and is communicated through face mask 14 to the air passages of the victim.

It is possible that excessive vacuum would have injurious effects to the victim. To forestall such effects, plunger 20 is fabricated from a flexible material which will yield and collapse or deflect under excessive vacuum, and configured so as to encourage this deflection should excessive vacuum develop in chamber 26. Deflection responds to attainment of a predetermined degree of vacuum, allowing air to bypass plunger 20 within cylinder 16 and to flow from chamber 28 into vacuum chamber 26, thereby relieving the hazardous condition.

Figure 2:
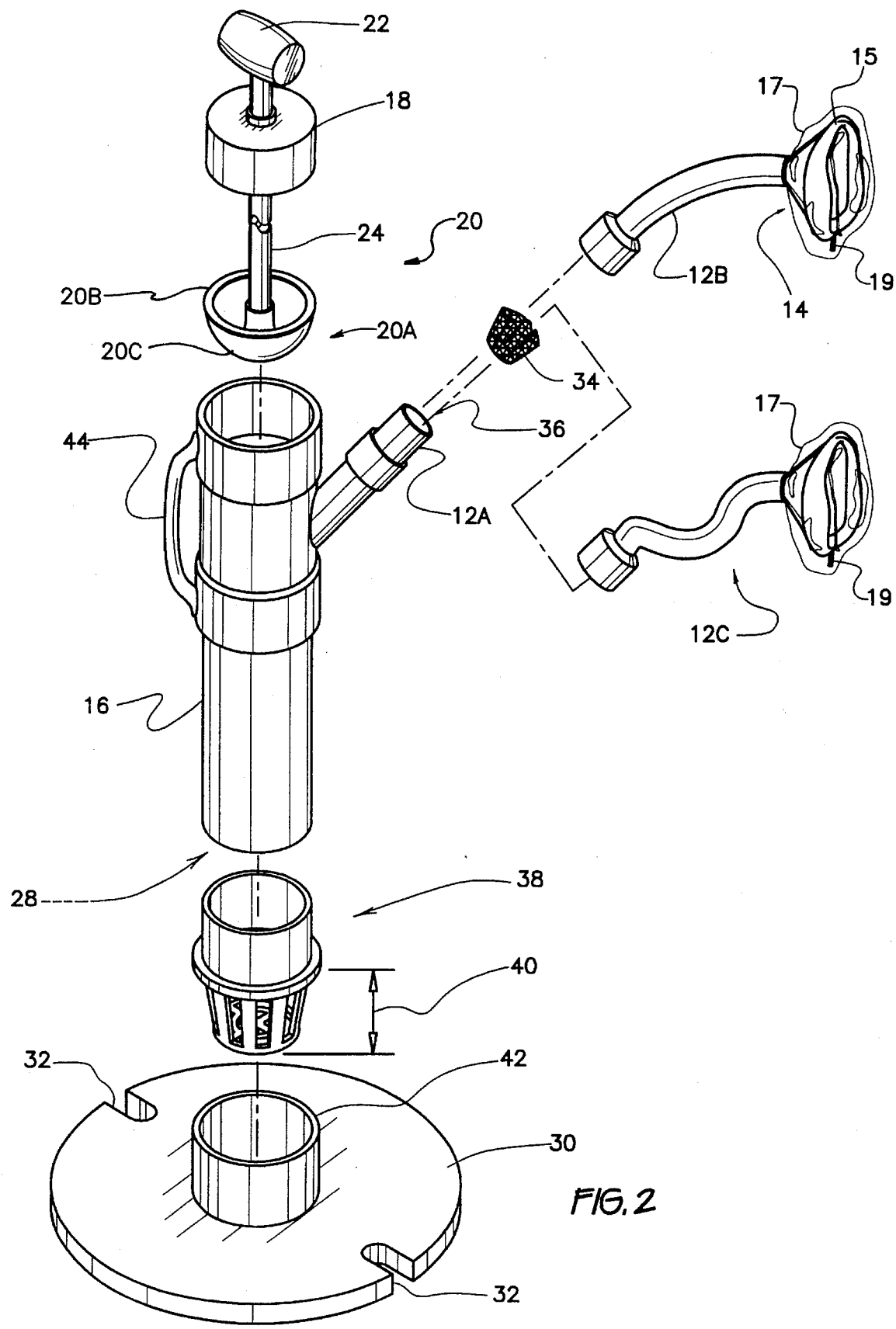
FIG. 2 is an exploded, perspective view of the invention, drawn to enlarged scale.

Referring both to FIGS. 1 and 2, plunger 20 will be seen to have a tapered skirt 20A including an expanded first section 20B characterized by a first circumference and a gathered second end 20C characterized by a second circumference which is smaller than that of first section 20B. Second end 20C faces the open distal end of cylinder 16, that being the end opposite that closed by cap 18.

Suction device 10 may be employed in several ways. In the embodiment of FIG. 1, it is intended that suction device 10 be stationary, mounted in a fixed position to an environmental surface such as a wall or floor (neither shown). This would be useful in places where choking is more apt to occur, such as in eating establishments. For this purpose, a base or flange 30 is attached to cylinder 16. Flange 30 has slots 32 or equivalent openings such as holes (not shown) for accepting projecting fasteners, such as studs, bolts, and screws.

In FIG. 1, device 10 has a neck comprising components 12A, 12B fabricated from a rigid material and extending above the level of cap 18. With face mask 14 supported rigidly in this location, and especially when secured to an environmental surface, device 10 promotes and enables self-administration of suction.

In other embodiments, flange 30 is deleted or simply not employed, in favor of suitable readily detachable brackets, hinges, or hooks, or may merely be propped on a firm supporting surface. Any of these arrangements enables ready portability of suction device 10 to an emergency site.

An advantage of fastening suction device 10 detachably to a solid surface is that this mounting enables ready self-administration of suction. The victim need not hold suction device 10 steady, but instead need only operate plunger 20 by handle 22. For this type of operation, face mask 14 is fabricated from a rigid material, such as polyvinyl chloride resin. Also, handle 22 extends above the level of cap 18, so that handle 22 is readily grasped by the victim when his or her face is pressed against face mask 14.

By incorporating detachable supports, suction device 10 is immediately portable, so that it can be carried to the site of a medical emergency by rescue personnel or by others. For this purpose, a neck comprising component 12A in combination with either component 12B or 12C is provided. Neck components 12B, 12C are fabricated from a flexible material, such as rubber or an equivalent synthetic resin, component 12A being rigid, and component 12C being flexible. FIG. 2 illustrates a suction device 10 having two neck components 12B, 12C, which are employed selectively, according to conditions of the situation at hand.

Frequently, a victim will be trapped in a poorly accessible location, or may be unconscious. Under these circumstances, it would not be feasible to hold the victim in an erect position as is possible for self-administration of suction. Rather, it is desired that a rescuer hold face mask 14 against the victim, and that this person or an assistant operate handle 22. A long, flexible neck 12C will allow suction device to be positioned as required for plunger operation, while still extending to a supine victim.

Suction device 10 is rendered more versatile by providing it as a kit incorporating a plurality of necks including a first neck portion 12B fabricated from a rigid material, and a second neck portion 12C fabricated from flexible material. Neck portions 12B and 12C are of different lengths, to provide versatility of reach of face mask 14.

Turning now to FIG. 2, certain internal components of suction device 10 will be discussed. One component is a strainer 34 for trapping the object (not shown) which formerly obstructed the breathing passage of the choking person, as that object is removed by suction. Neck sections 12A and 12B separate at a joint indicated at 36. Strainer 34 is entrapped at joint 36.

A grate 38 is friction fit at the distal end of cylinder 16. Grate 38 prevents large objects from entering into chamber 28 of cylinder 16, and thereby potentially obstructing plunger 20. Grate 38 has a depth dimension, shown at 40, rather than comprising a perforated, planar member. This construction of grate 38 supports cylinder 16 spaced apart from and above a soft or yielding surface, such as soft ground or even a carpet, or when held and cradled against the body during self-administration of suction. Therefore, egress of air from chamber 28 is not obstructed during the downstroke of plunger 20.

Flange or base 30 cooperates with cylinder 16 and grate 38 by including a socket 42, for separably supporting cylinder 16 as a free standing unit. Cylinder 16 may be instantly withdrawn from socket 42 when desired. For example, cylinder 16 may be removed from a permanent mounting location in order to be transported temporarily to another location.

A handle 44 is attached to cylinder 16, for convenience in carrying and transporting suction device 10.

A suction device 100 lacking a neck is shown in FIG. 3. The general construction of device 100 is similar to that of device 10, except that strainer 34 (see FIG. 2) must be housed within cylinder 116, since there is no neck in this embodiment. This embodiment enables placement of cylinder 116 closer to the victim's face than is normally practiced with device 10 (see FIG. 1).

An embodiment of the invention illustrated in FIG. 4 reverses arrangement of the operating handle from that of device 100 of FIG. 3. In other respects, suction device 200 of FIG. 4 includes generally similar structure and function of device 100 of FIG. 3. In device 200, handle 202 is drawn away from cylinder 216 when operating. It will be seen that plunger 220 retains a configuration enabling air to bypass plunger 220 in the event of excessive vacuum. Device 200, if fixed to a vertical environmental surface, is particularly ergonomically advantageous for self-administration of vacuum.

Devices 100 and 200, of FIGS. 3 and 4 respectively, employ the same face mask 14 as does device 10 of FIG. 1. Devices 100 and 200 are provided with projections (not shown) or equivalent structure enabling a face mask 14 to be attached to respective cylinders 116 and 216 in the same manner as by slipping one end of a face mask 14 over a neck portion 12B or 12C (see FIG. 2) of suction device 10.

It is to be understood that the present invention is not limited to the embodiments described above, but encompasses any and all embodiments within the scope of the following claims.

I claim:

1. A suction device for clearing an object obstructing the breathing passage of a choking victim, said suction device comprising:

vacuum generating means for manually generating vacuum, said vacuum generating means comprising a cylinder assembly having a cylinder including a proximal end, a cap sealing said proximal end, and an open distal end, and a plunger slidably disposed within said cylinder, said plunger having an upper side facing said cap, a lower side facing said open distal end of said cylinder, and a rod passing through said cap, said plunger dividing said cylinder into an upper chamber located between said upper side of said plunger and said cap, and a lower chamber located between said lower side of said plunger and said distal open end of said cylinder, a handle attached to said rod and disposed outside said cylinder, said handle accessible to a user, whereby downward movement of said plunger towards said distal open end of said cylinder generates vacuum within said upper chamber of said cylinder and whereby vacuum may be communicated through said face mask to the mouth of a person choking on an object, such that vacuum draws the object from the breathing passage of the choking person, and said plunger being entirely fabricated from a flexible material which deflects responsive to a pressure differential existing between said upper chamber and said lower chamber when a predetermined degree of vacuum is developed, whereby said plunger provides means for limiting vacuum generated within said cylinder;

a face mask connected to said vacuum generating means, said face mask having a flexible, circular member for placing over a person's mouth and nose and excluding communication between the person's air passages and the ambient atmosphere; and means for establishing fluid communication of vacuum between said vacuum generating means and said face mask.

2. The suction device according to claim 1, further comprising a grate for preventing entry of a foreign object into said lower chamber of said cylinder, said grate disposed at said distal open end of said cylinder.

3. The suction device according to claim 1, further comprising a strainer disposed between said face mask and said cylinder, for trapping the object formerly obstructing the breathing passage of the choking person when the object is removed by suction and drawn past said face mask of said suction device, said strainer disposed within said neck.

4. The suction device according to claim 1, further comprising mounting means for mounting said suction device to an external environmental surface in a fixed position on the external environmental surface.

5. The suction device according to claim 4, said mounting means comprising a flange mounted to said cylinder, said flange having means defining an opening for accepting a projecting fastener.

6. The suction device according to claim 1, said plunger having a tapered skirt having an expanded first section characterized by a first circumference and a gathered second end characterized by a second circumference which is smaller than that of said first section, said second end facing said open distal end of said cylinder, whereby deflection of said skirt is promoted responsive to development of excessive vacuum within said upper chamber of said cylinder.

7. The suction device according to claim 1, said means for establishing fluid communication of vacuum further comprising a neck communicating between said vacuum generating means and said face mask, whereby reach of said suction device is extended.

8. The suction device according to claim 7, wherein said neck is fabricated from a rigid material.

9. The suction device according to claim 7, wherein said neck is fabricated from a flexible material.

10. The suction device according to claim 7, said neck comprising a plurality of necks, including a first neck fabricated from a rigid material, and a second neck fabricated from a flexible material.

11. The suction device according to claim 7, said neck comprising a plurality of necks of different lengths from one another.

12. The suction device according to claim 1, said neck being fabricated from a rigid material and extending from said cylinder to a point beyond the level of said cap of said cylinder, whereby self-administration of suction is promoted.

13. A suction device for clearing an object obstructing the breathing passage of a choking victim, said suction device comprising:

a cylinder assembly for generating vacuum, said cylinder assembly having a cylinder including a proximal end, a cap sealing said proximal end, and an open distal end, and a plunger slidably disposed within said cylinder, said plunger having an upper side, a lower side, and a rod passing through said cap, said plunger dividing said cylinder into an upper chamber located above said upper side of said plunger and a lower chamber located below said lower side of said plunger, a handle attached to said rod and disposed outside said cylinder, said handle accessible to a user; and connection means for connecting the nose and mouth of a user to vacuum generated by said cylinder assembly, said connection means comprising a face mask having a flexible, circular member for placing over a person's nose and mouth and excluding communication between the person's nose and mouth, and the ambient atmosphere, and a plurality of necks each individually attachable to said cylinder assembly and when attached, communicating between said upper chamber of said cylinder and said face mask, whereby downward movement of said plunger generates vacuum within said upper chamber of said cylinder, and said vacuum is communicated through said neck and said face mask to the nose and mouth of a victim choking on an object, such that said vacuum draws the object from the breathing passage of the choking victim, one neck being fabricated from a rigid material for enabling self-administration of suction, and another neck being fabricated from a flexible material, for adjustable positioning on a choking victim, each said neck having a strainer disposed therein, for trapping the object formerly obstructing the breathing passage of the choking victim when the object is removed by suction and drawn into said neck of said suction device.

14. The suction device according to claim 13, further comprising a grate for preventing entry of a foreign object into said lower chamber of said cylinder.

15. The suction device according to claim 13, said neck being fabricated from a rigid material extending from said cylinder to a point beyond the level of said cap of said cylinder, whereby self-administration of suction is promoted.

16. The suction device according to claim 13, further comprising mounting means for mounting said suction device to an external environmental surface in a fixed position on the external environmental surface, said mounting means comprising a flange mounted to said cylinder, said flange having means defining an opening for accepting a projecting fastener, and means defining a socket for removably supporting said cylinder by said flange.

* * * * *